(12) United States Patent
Xing et al.

(10) Patent No.: US 12,312,292 B2
(45) Date of Patent: May 27, 2025

(54) LONG CHAIN ALKYL ESTERAMINE LIPID COMPOUND, PREPARATION METHOD THEREFOR AND APPLICATION THEREOF IN NUCLEIC ACID DELIVERY

(71) Applicants: RinuaGene Biotechnology Co., Ltd., Jiangsu (CN); RinuaGene International HK Limited, Hong Kong (CN)

(72) Inventors: Rui Xing, Suzhou (CN); Kai Lv, Suzhou (CN); Shan Cen, Suzhou (CN); Yijie Dong, Suzhou (CN)

(73) Assignees: RINUAGENE BIOTECHNOLOGY CO., LTD., Jiangsu (CN); RINUAGENE INTERNATIONAL HK LIMITED, Hong Kong (CN)

( * ) Notice: Subject to any disclaimer, the term of this patent is extended or adjusted under 35 U.S.C. 154(b) by 0 days.

(21) Appl. No.: 18/476,222

(22) Filed: Sep. 27, 2023

(65) Prior Publication Data

US 2024/0018094 A1 Jan. 18, 2024

Related U.S. Application Data

(63) Continuation of application No. PCT/CN2023/095040, filed on May 18, 2023.

(30) Foreign Application Priority Data

May 19, 2022 (CN) .................. 202210546254.8
Jul. 26, 2022 (CN) .................. 202210884245.X

(51) Int. Cl.
C07C 229/16 (2006.01)
A61K 47/18 (2017.01)

(52) U.S. Cl.
CPC .......... *C07C 229/16* (2013.01); *A61K 47/183* (2013.01); *C07C 2601/02* (2017.05); *C07C 2601/04* (2017.05)

(58) Field of Classification Search
None
See application file for complete search history.

(56) References Cited

U.S. PATENT DOCUMENTS 10,730,924 B2    8/2020    Ticho et al.
10,857,105 B2    12/2020    Benenato et al.
(Continued)

FOREIGN PATENT DOCUMENTS

CN    101646645 A    2/2010
CN    109640962 A    4/2019
(Continued)

OTHER PUBLICATIONS

International Search Report mailed on Aug. 18, 2023, in counterpart PCT Application No. PCT/CN2023/095040.
(Continued)

*Primary Examiner* — Sudhakar Katakam
*Assistant Examiner* — Jennifer C Sawyer
(74) *Attorney, Agent, or Firm* — Panitch Schwarze Belisario & Nadel LLP; Erin M. Dunston

(57) ABSTRACT

The present invention relates to a long chain alkyl esteramine lipid compound as shown in Formula I, preparation method therefor as well as use thereof in nucleic acid delivery, the long chain alkyl esteramine lipid compound provided by the present invention has an excellent encapsulation rate and delivery effect as a lipid molecule in delivering disease treatment or preventive agents, showing lower toxicity and certain tissue distribution characteristics, and providing a basis of more selections for delivering disease therapeutic or prophylactic agents.

(Continued)

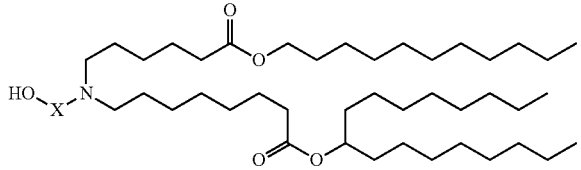

Formula (I)

3 Claims, 5 Drawing Sheets

(56) References Cited

U.S. PATENT DOCUMENTS

| | | | |
|---|---|---|---|
| 10,993,918 | B2 | 5/2021 | Martini et al. |
| 11,464,848 | B2 | 10/2022 | Ciaramella et al. |
| 2018/0371047 | A1 | 12/2018 | Ticho et al. |
| 2019/0175517 | A1 | 6/2019 | Martini et al. |
| 2019/0314292 | A1* | 10/2019 | Benenato ............... C07C 251/38 |
| 2020/0129608 | A1 | 4/2020 | Ciaramella et al. |
| 2020/0354429 | A1 | 11/2020 | Ticho et al. |
| 2021/0154148 | A1 | 5/2021 | Benenato et al. |
| 2022/0009878 | A1 | 1/2022 | Parmar et al. |
| 2022/0071915 | A1 | 3/2022 | Martini et al. |
| 2022/0409536 | A1 | 12/2022 | Benenato et al. |
| 2023/0114180 | A1 | 4/2023 | Ciaramella et al. |

FOREIGN PATENT DOCUMENTS

| | | |
|---|---|---|
| CN | 110520409 A | 11/2019 |
| CN | 113018449 A | 6/2021 |
| CN | 113039174 A | 6/2021 |
| CN | 114213295 A | 3/2022 |
| CN | 115073316 A | 9/2022 |
| CN | 115521220 A | 12/2022 |
| WO | WO-2008118494 A2 | 10/2008 |
| WO | WO-2017201349 A1 | 11/2017 |
| WO | WO-2018170260 A1 | 9/2018 |
| WO | WO-2020061367 A1 | 3/2020 |
| WO | WO-2021142280 A1 | 7/2021 |

OTHER PUBLICATIONS

First Office Action & Search Report for CN202210884245X issued on Sep. 29, 2022.

First Office Action & Search Report for CN202210546254.8 issued on Mar. 11, 2023.

\* cited by examiner

LONG CHAIN ALKYL ESTERAMINE LIPID COMPOUND, PREPARATION METHOD THEREFOR AND APPLICATION THEREOF IN NUCLEIC ACID DELIVERY

CROSS-REFERENCE TO RELATED APPLICATIONS

This application is a "bypass" continuation of International Patent Application PCT/CN2023/095040, filed on May 18, 2023, which claims priority to Chinese Patent Application 202210884245.X, filed on Jul. 26, 2022, and Chinese Patent Application No. 202210546254.8, filed May 19, 2022, all of which are incorporated herein by reference in their entireties for all purposes.

TECHNICAL FIELD

The present invention relates to the field of pharmaceutical technologies, in particular to a long chain alkyl esteramine lipid compound, preparation method therefor, and use thereof in the delivery of therapeutic and/or prophylactic agent(s).

BACKGROUND

Nucleic acids synthesized by in vitro transcription technologies are transported into tissue cells by lipid nanoparticle delivery systems, to further translated to target proteins by their own cellular translation systems, which act as antigens to stimulate immune responses or supplement missing proteins in cells to perform functions thereof, and finally achieve a purpose of treatment. Nucleic acid-based treatment technologies have advantages of rapid preparation, low cost, safety, etc., making them stand out among many treatment methods, and be widely used in treatment of cancers, infectious diseases and rare diseases. However, since nucleic acids are inherently unstable and easily degraded in vivo, a choice of stable delivery system is the key to the development of this class of drugs.

With the vigorous development of nanoliposome technologies, researchers are committed to developing new synthetic lipids and improving the drug-carrying capacity of liposomes, cationic lipids have emerged for the effective reproduction of negatively charged drugs, consequently, especially for the delivery of nucleic acid drugs. A cationic lipid generally has a positively charged head group connected to a hydrophobic tail fragment (cholesterol or fatty chain) by a linking bond (amide, ester, or ether bond), and the structure thereof is an important factor determining the efficacy of nucleic acid drugs. In recent years, it has been greatly developed in lipid molecules, from permanently charged cationic lipid molecules (e.g., DOTAP, DOGS (structural formula as shown below), etc., to an ionizable cationic lipid Dlin-DMA. MC3 (structural formula as shown below) was obtained by modification of chain length and substitution position based on DLin-DMA. At present, a small number of cation delivery molecules have been applied to the clinic and marketed. The world's first siRNA drug, Onpattro, was approved in 2018 for the treatment of nerve damage caused by thyretin amyloidosis, and the key lipid molecule used in this drug is MC3. Based on the optimization of MC3, Moderna acquired the lipid molecule SM-102 (structural formula as shown below) with hydroxyethyl attached to the nitrogen atom, and applied the compound to the development of a vaccine for COVID-19, which was authorized by the FDA on Dec. 8, 2020. There have also been reports in the literature that lipid molecules in LNP can induce inflammatory responses in vivo (Nature Immunology|VOL 23 p 532-542).

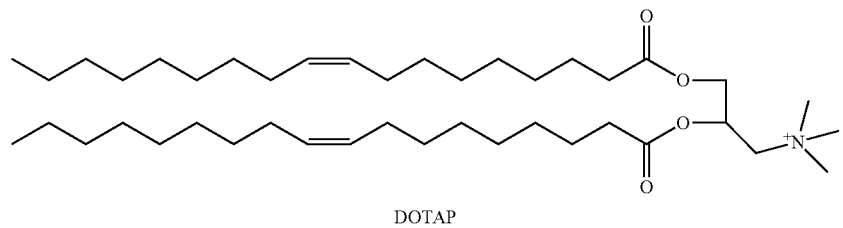

DOTAP

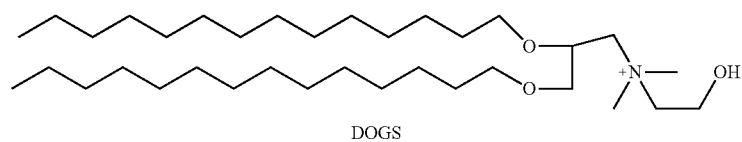

DOGS

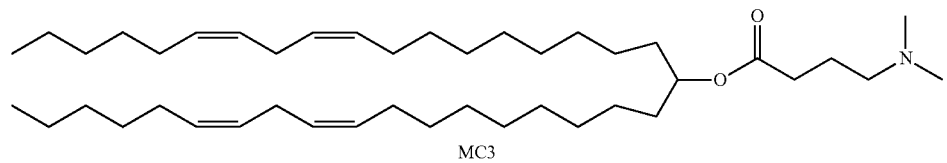

MC3

-continued

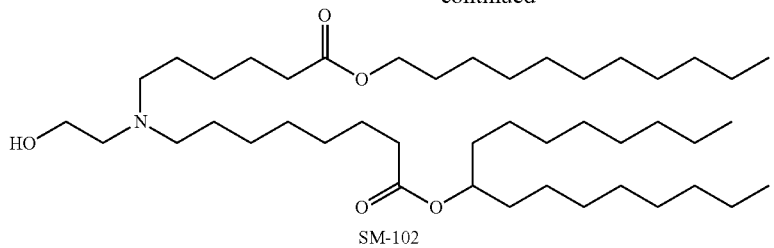
SM-102

In view of advantages of ionizable lipid molecule delivery, it has become more promising in research and development of different types of targeted delivery molecules to increase the accumulation of drugs in the targeted organs. Our team has developed a series of new lipid molecular compounds. Lipid molecules have excellent encapsulation rate and delivery effect in delivering disease treatment or prophylactic agents, while exhibiting low toxicity and certain tissue distribution features.

SUMMARY

One object of the present invention is to provide a series of long chain alkyl esteramine lipid compounds.

Another object of the present invention is to provide a method for preparing long chain alkyl esteramine lipid compounds.

Another object of the present invention is to provide a composition comprising a long chain alkyl esteramine lipid compound.

Another object of the present invention is to provide use of a long chain alkyl esteramine lipid compound as lipid molecule in nucleic acid delivery.

Definitions

The terms used herein for the description of the present invention are only intended to describe specific embodiments and are not intended as limitations on the present invention. The nomenclature used herein and laboratory operations in organic chemistry, medicinal chemistry, and biology as described herein are well known and commonly used in the art. Unless otherwise mentioned, all technical and scientific terms used herein have the same meaning as those generally understood by those skilled in the technical field to which the art belongs.

As used in embodiments of the present invention and the description of the appended claims, the singular form "a", "an", "the", "its" is used to refer to the singular and plural of the article, unless the context expressly refers to otherwise. For example, a compound includes one or more compounds.

As used herein, "and/or" means and includes any and all possible combinations of one or more related listed items.

As used herein, the term "disease" or "diseases" refers to any alteration of the state of the body or some organ that interrupts or interferes with the performance of its function and/or causes symptoms.

As used herein, the term "treatment" or "therapeutic" aims to alleviate or eliminate disease state or condition to which it is intended. A subject is successfully "treated" if the subject exhibits observable and/or detectable alleviation or improvement on one or more indications and symptoms after receiving a therapeutically effective amount of the compound or a pharmaceutically acceptable salt, stereoisomer, polymorph, solvent, isotope marker, metabolite or prodrug thereof, or a pharmaceutical composition thereof in accordance with the method as described herein. It should also be understood that the treatment of the disease state or condition includes not only complete treatment, but also incomplete treatment, but achieving some biological or medically relevant results.

As used herein, the "linear alkane" or "branched alkane" of "X is $C_5$-$C_{12}$ linear alkane or $C_2$-$C_{12}$ branched or linear alkane substituted by $R^1$ and $R^2$" may be interpreted as linear or branched alkylene group. Examples of alkylene group include, but are not limited to, linear or branched $C_{2-12}$ alkylene, $C_{5-12}$ alkylene, $C_{2-8}$ alkylene, e.g., $—(CH_2)_2—$, $—(CH_2)_3—$, $—(CH_2)_4—$, $—(CH_2)_5—$, $—(CH_2)_6—$, $—(CH_2)_7—$, $—(CH_2)_8—$, $—CH(CH_3)—(CH_2)_2—$, $—CH(CH_3)—(CH_2)_3—$.

Technical Subject I

The present invention provides a long chain alkyl esteramine lipid compound having a structure as shown in Formula I, or a stereoisomer, polymorph, solvate, isotope marker, metabolite, prodrug or a pharmaceutical salt thereof:

Formula I

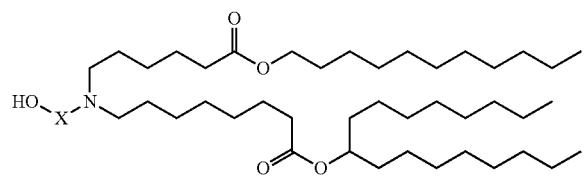

Wherein, X is $C_5$-$C_{12}$ linear alkane or $C_2$-$C_{12}$ branched or linear alkane substituted by $R^1$ and $R^2$;

$R^1$ is selected from the group consisting of $C_1$-$C_5$ linear or branched alkyl, $C_2$-$C_5$ linear or branched alkenyl, $C_3$-$C_5$ cycloalkyl, mono- or polyhalogenated $C_1$-$C_3$ alkyl, and halogen;

$R^2$ is independently selected from the group consisting of $C_1$-$C_5$ linear alkyl, halogen and H;

$R^1$ and $R^2$ may be bonded to the same or different carbon atoms, and when $R^1$ and $R^2$ are bonded to the same carbon atom, $R^1$ and $R^2$ are independent substituents, or $R^1$ and $R^2$, taken together with the carbon atom to which they are bonded, form a ring.

In some preferred embodiments of the present invention, X is $C_5$-$C_{12}$ linear alkane.

In some preferred embodiments of the present invention, X is $C_2$-$C_{12}$ branched or linear alkane substituted by $R^1$ and $R^2$; wherein $R^1$ is selected from the group consisting of $C_1$-$C_5$ linear or branched alkyl, $C_2$-$C_5$ linear or branched alkenyl, $C_3$-$C_5$ cycloalkyl, mono- or polyhalogenated $C_1$-$C_3$ alkyl, and halogen;

$R^2$ is independently selected from the group consisting of $C_1$-$C_5$ linear alkyl, halogen, and H;

$R^1$ and $R^2$ may be bonded to the same or different carbon atoms, and when $R^1$ and $R^2$ are bonded to the same carbon atom, $R^1$ and $R^2$ are independent substituents, or $R^1$ and $R^2$, taken together with the carbon atom to which they are bonded, form a ring.

In some preferred embodiments of the present invention, the $R^1$ is selected from the group consisting of methyl, ethyl, isopropyl, n-propyl, cyclopropyl, halogen, difluoromethyl and trifluoromethyl.

In some preferred embodiments of the present invention, the $R^2$ is selected from the group consisting of methyl, ethyl, halogen and H.

In some preferred embodiments of the present invention, the halogen is selected from F or Cl.

In some preferred embodiments of the present invention, when $R^1$ and $R^2$ are bonded to the same carbon atom, $R^1$ and $R^2$, taken together with the carbon atom to which they are bonded, form a ring, preferably a three-membered ring or a four-membered ring.

In some preferred embodiments of the present invention, when $R^1$ and $R^2$ are bonded to different carbon atoms, $R^1$ is methyl, and $R^2$ is hydrogen.

In some preferred embodiments of the present invention, the compound includes the following structures:

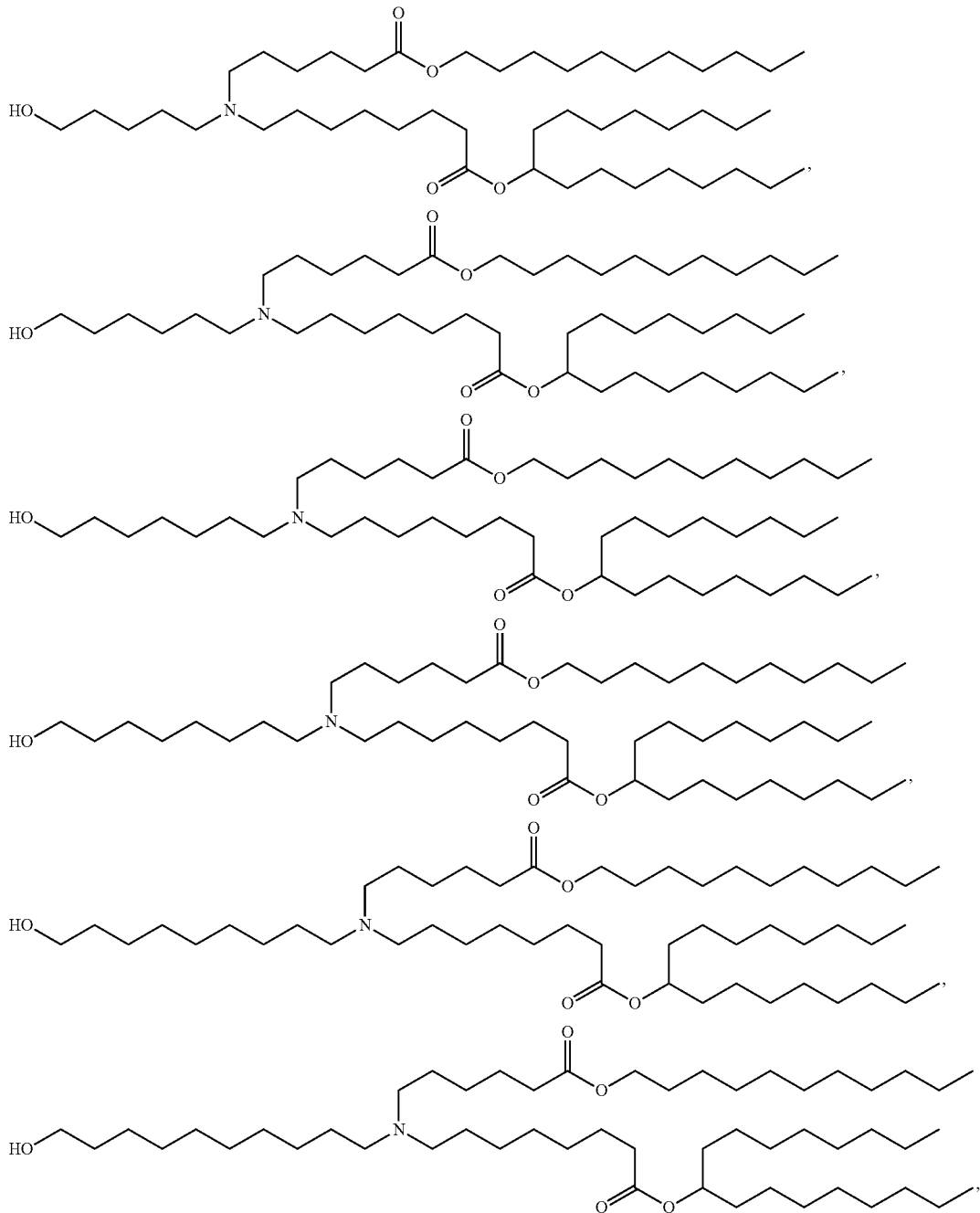

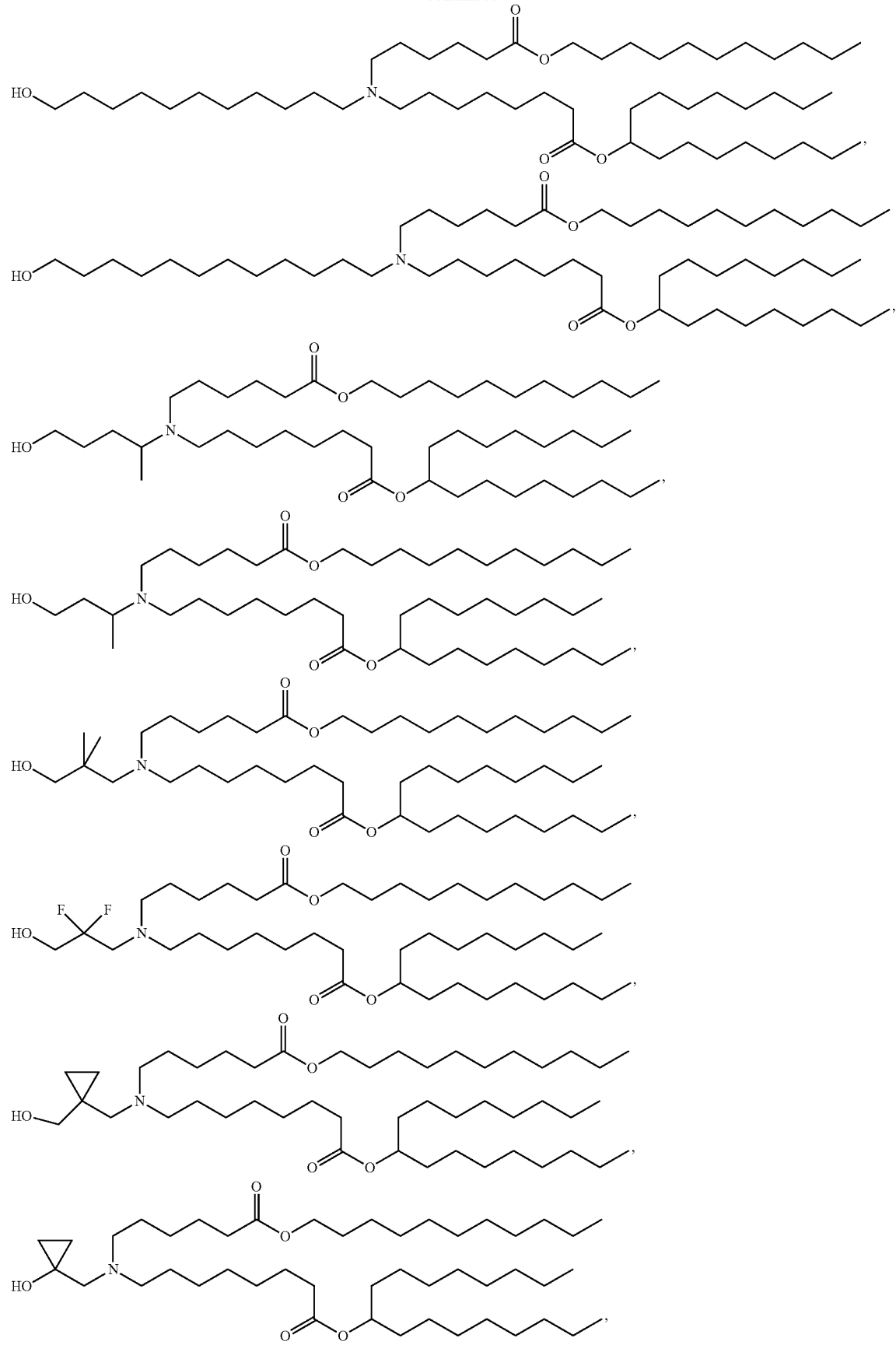

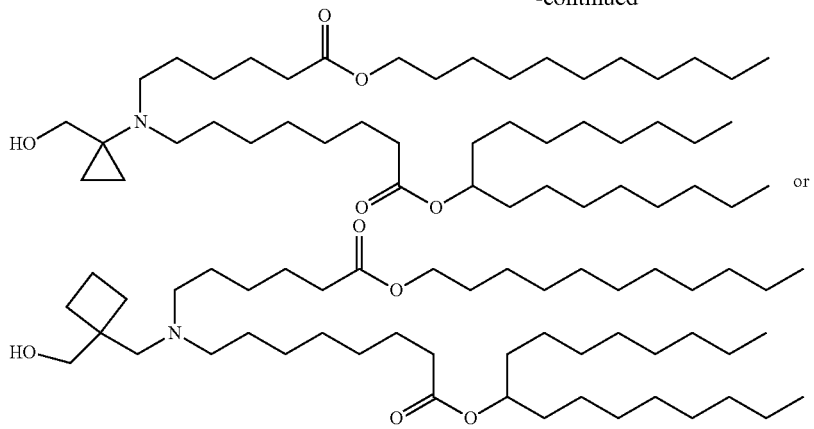

or a stereoisomer, polymorph, solvate, isotope marker, metabolite, prodrug or a pharmaceutically acceptable salt thereof.

Technical Subject II

The present invention also provides a method for synthesizing the compound as shown in formula I.

The following steps are included:

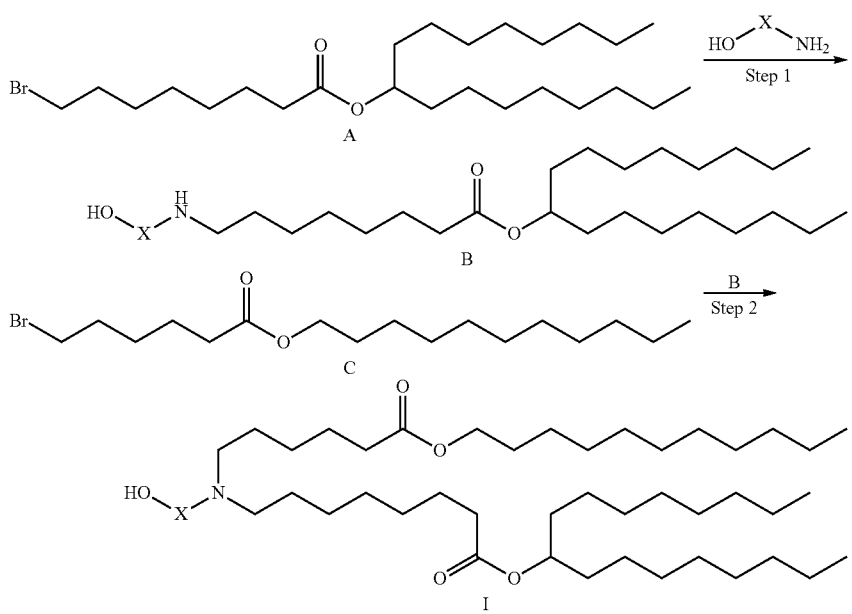

Step 1: To a solution of compound A in a protic solvent were added OH—X—NH$_2$ and DIEA, the reaction was heated for 12~36 hours, and then diluted with water, extracted with ethyl acetate, and purified to obtain compound B; and Step 2: To a solution of compound C in an aprotic solvent were added compound B, potassium carbonate and potassium iodide, the reaction was heated for 24~48 hours, and then diluted with water, extracted with ethyl acetate, and purified to obtain compound of formula I.

Further, the solvent of step 1 is ethanol or propanol.

Further, the solvent of step 2 is a mixed solvent of 2-methyltetrahydrofuran and acetonitrile, or a mixed solvent of cyclopentyl methyl ether and acetonitrile, and the 2-methyltetrahydrofuran or cyclopentyl methyl ether is mixed with acetonitrile in a ratio of 1:1 to 3:1.

Further, the purification is the purification by silica gel column chromatography.

Technical Subject III

The present invention provides a composition comprising a therapeutic or prophylactic agent and a pharmaceutically acceptable carrier for delivering the therapeutic or prophylactic agent, wherein the pharmaceutically acceptable carrier comprises the long chain alkyl esteramine lipid compound, or a stereoisomer, polymorph, solvate, isotope marker, metabolite, prodrug or a pharmaceutically acceptable salt thereof according to technical subject I.

Further, the therapeutic or prophylactic agent includes one or more of a nucleic acid molecule, protein, peptide, or small molecule compound.

Further, the nucleic acid includes any form of nucleic acid molecules, including but not limited to a single-stranded DNA, double-stranded DNA, short isomer, agomir, antagomir, antisense molecule, small interfering RNA (siRNA), asymmetric interfering RNA (aiRNA), microRNA (miRNA), Dicer-substrate RNA (dsRNA), small hairpin RNA (shRNA), transfer RNA (tRNA), messenger RNA (mRNA) and other forms of RNA molecules known in the art, or nucleic acid mimics such as lock-nucleic acid (LNA), peptide nucleic acid (PNA), and morpholinocyclic oligonucleotides.

Further, the nucleic acid is selected from at least one mRNA encoding an antigen or a fragment or epitope thereof.

Further, the therapeutic or prophylactic agent is a vaccine.

Further, the small molecule compound may be selected from the group consisting of antineoplastic drugs, anti-infectives, antidepressants, anticonvulsants, antibiotics/antimicrobials, antifungals, antiparasitic drugs, immunomodulators or anesthetics.

Further, the "pharmaceutical composition" may further includes other excipients, for example, diluents, fillers, binders, disintegrants, lubricants, glidants, granulating agents, coating agents, wetting agents, solvents, co-solvents, suspending agents, emulsifiers, sweeteners, flavorings, masking agents, colorants, anti-caking agents, moisturizers, chelating agents, plasticizers, tackifiers, antioxidants, preservatives, stabilizers, surfactants and buffers.

The compound of the present invention and a pharmaceutically acceptable salt thereof may be formulated into ordinary preparations, sustained-release preparations, controlled-release preparations, targeting preparations and various microparticle drug delivery systems.

Technical Subject IV

The present invention also provides use of the compound shown in formula I, or a stereoisomer, polymorph, solvate, isotope marker, metabolite, prodrug or a pharmaceutically acceptable salt thereof in the manufacture of a nucleic acid drug, vaccine, protein or peptide drug, or a small molecule drug.

Further, the use is the use in the manufacture of a nucleic acid delivering drug, wherein the nucleic acid, includes but not limited to a single-stranded DNA, double-stranded DNA, short isomer, agomir, antagomir, antisense molecule, small interfering RNA (siRNA), asymmetric interfering RNA (aiRNA), microRNA (miRNA), Dicer-substrate RNA (dsRNA), small hairpin RNA (shRNA), transfer RNA (tRNA), messenger RNA (mRNA) and other forms of RNA molecules known in the art, or nucleic acid mimics such as lock-nucleic acid (LNA), peptide nucleic acid (PNA), and morpholinocyclic oligonucleotides.

Further, the nucleic acid is selected from at least one mRNA encoding an antigen or a fragment or epitope thereof.

Further, the use is the use in the manufacture of mRNA drugs.

Further, the use is the use in the manufacture of mRNA vaccines.

Further, the use is the use in the manufacture of antineoplastic drugs, anti-infectives, antidepressants, anticonvulsants, antibiotics/antimicrobials, antifungals, antiparasitic drugs, immunomodulators or anesthetics.

Technical Subject V

The present invention also provides the compound as shown in Formula I, or a stereoisomer, polymorph, solvate, isotope marker, metabolite, prodrug or a pharmaceutically acceptable salt thereof, for use as a pharmaceutically acceptable carrier for delivering a therapeutic or prophylactic agent.

Further, the therapeutic or prophylactic agent includes one or more of a nucleic acid molecule, peptide, protein, vaccine, or a small molecule drug.

Further, the nucleic acid molecule includes, but not limited to a single-stranded DNA, double-stranded DNA, short isomer, agomir, antagomir, antisense molecule, small interfering RNA (siRNA), asymmetric interfering RNA (aiRNA), microRNA (miRNA), Dicer-substrate RNA (dsRNA), small hairpin RNA (shRNA), transfer RNA (tRNA), messenger RNA (mRNA) and other forms of RNA molecules known in the art, or nucleic acid mimics such as lock-nucleic acid (LNA), peptide nucleic acid (PNA), and morpholinocyclic oligonucleotides.

Further, the nucleic acid molecule is selected from at least one mRNA encoding an antigen or a fragment or epitope thereof.

Further, the therapeutic or prophylactic agent is a vaccine.

Further, the vaccine includes an mRNA vaccine.

Further, the small molecule drug may be selected from the group consisting of antineoplastic drugs, anti-infectives, antidepressants, anticonvulsants, antibiotics/antimicrobials, antifungals, antiparasitic drugs, immunomodulators or anesthetics.

Technical Subject VI

The present invention also provides use of the compound shown in Formula I, or a stereoisomer, polymorph, solvate, isotope marker, metabolite, prodrug or a pharmaceutically acceptable salt thereof, for delivering a therapeutic or prophylactic agent.

Further, the therapeutic or prophylactic agent includes one or more of a nucleic acid molecule, peptide, protein, vaccine, or a small molecule drug.

Further, the nucleic acid molecule includes, but not limited to a single-stranded DNA, double-stranded DNA, short isomer, agomir, antagomir, antisense molecule, small interfering RNA (siRNA), asymmetric interfering RNA (aiRNA), microRNA (miRNA), Dicersubstrate RNA (dsRNA), small hairpin RNA (shRNA), transfer RNA (tRNA), messenger RNA (mRNA) and other forms of RNA molecules known in the art, or nucleic acid mimics such as lock-nucleic acid (LNA), peptide nucleic acid (PNA), and morpholinocyclic oligonucleotides.

Further, the nucleic acid molecule is selected from at least one mRNA encoding an antigen or a fragment or epitope thereof.

Further, the therapeutic or prophylactic agent is a vaccine.

Further, the vaccine includes an mRNA vaccine.

Further, the small molecule drug may be selected from the group consisting of antineoplastic drugs, anti-infectives, antidepressants, anticonvulsants, antibiotics/antimicrobials, antifungals, antiparasitic drugs, immunomodulators and anesthetics.

The beneficial effects of the present invention are as follows:

The present invention provides a new class of long chain alkyl esteramine lipid compounds. Through a large number of studies and experimental verification, it is discovered that the long chain alkyl esteramine lipid compounds have the features of high encapsulation rate, good delivery effect, good safety and relative selection distribution, which provide more selection basis for the delivery of disease therapeutic or prophylactic agents.

BRIEF DESCRIPTION OF THE DRAWINGS

In order to more clearly illustrate the specific embodiments of the present invention or the technical solution in the prior art, the following will be briefly introduced to the drawings required in the specific embodiment or prior art description.

DETAILED DESCRIPTION

Figure 1:
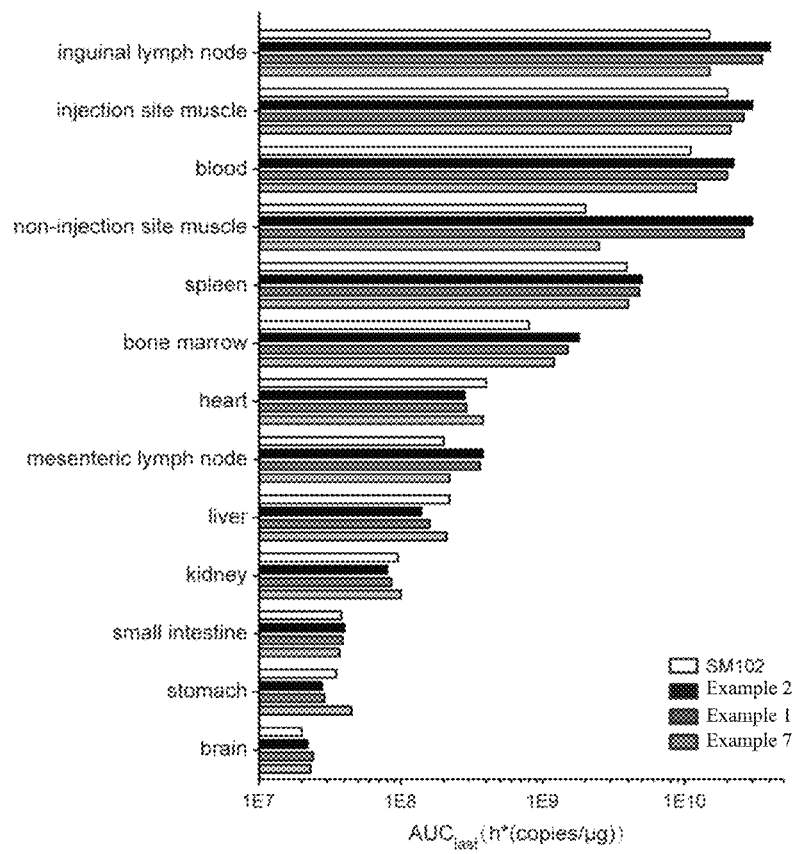
FIGS. 1 and 2 illustrate distribution of delivered mRNA in vivo.

The present invention is described below in conjunction with specific embodiments, which are not intended to limit the scope of the present invention, but to provide guidance for those skilled in the art to prepare and use the compounds and compositions of the present invention. The chemical names of the compounds described in this application are usually generated by ChemDraw Ultra (ChambridgeSoft) and/or generally follow the principles of IUPAC nomenclature.

The synthesis route of the compounds in the present embodiments is as follows:

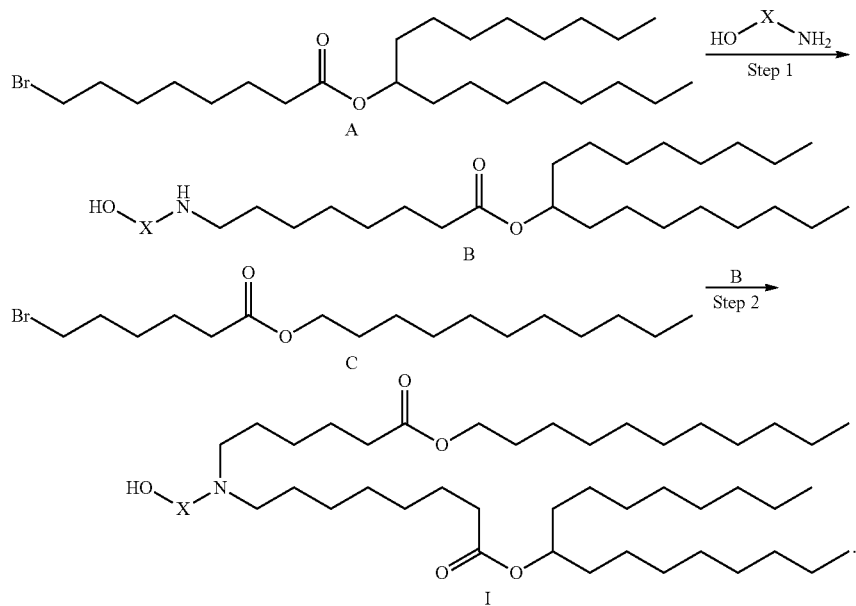

Example 1

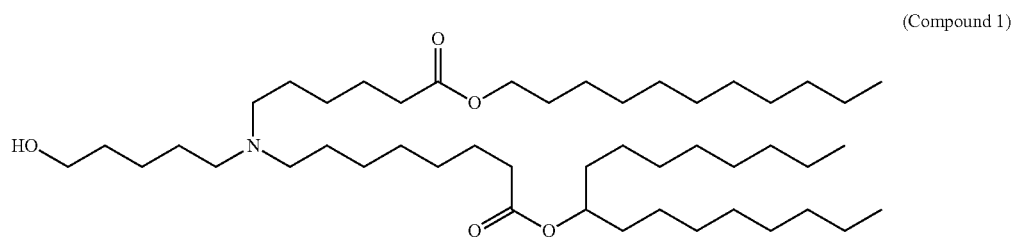 [SMILES: CCCCCCCCCCCOC(=O)CCCCCN(CCCCCO)CCCCCCCC(=O)OC(CCCCCCCC)CCCCCCCC]

5-amino-1-pentanol (88 mg, 0.86 mmol) and DIEA (213 μL, 1.29 mmol) were added to the solution of compound A (200 mg, 0.43 mmol) in ethanol (5 mL), heated at reflux for 20 hours, and the reaction was monitored by TLC. The reaction was cooled to room temperature after it was complete. An equal volume of water was added to the reaction solution for dilution, followed by ethyl acetate extraction (10 mL×3), concentration, and silica gel column chromatography (dichloromethane:methanol=10:1), to obtain compound B-1, X=$(CH_2)_5$ (172 mg, yield 82.69%).

5-fold equivalent compounds C (936 mg, 2.69 mmol), $K_2CO_3$ (224 mg, 1.62 mmol), and KI (90 mg, 0.54 mmol) were added to the solution of compound B-1 (260 mg, 0.54 mmol) in a mixed solvent of acetonitrile and cyclopentyl methyl ether (cyclopentyl methyl ether:acetonitrile=2:1, 3 mL), then heated at 90° C. for 24 hours. The reaction was monitored by TLC, and cooled to room temperature after it was complete. The reaction solution was diluted with water, then extracted with ethyl acetate (10 mL×3), concentrated, and chromatographed by silica gel column (dichloromethane:methanol=20:1) to obtain oil compound 1 (140 mg, yield 34.5%): $^1$H NMR (500 MHz, CDCl$_3$) δ 4.88-4.83 (m, 1H), 4.05 (t, J=6.7 Hz, 2H), 3.63 (t, J=6.3 Hz, 2H), 2.85-2.58 (brs, 6H), 2.32-2.23 (m, 4H), 1.73-1.57 (m, 13H), 1.52-1.41 (m, 5H), 1.38-1.25 (m, 50H), 0.87 (t, J=6.8 Hz, 9H); $^{13}$C NMR (126 MHz, CDCl$_3$) δ 173.77, 173.60, 74.23, 64.61, 62.13, 53.26, 53.11, 34.64, 34.17, 34.11, 32.07, 31.94, 31.90, 31.88, 29.63, 29.56, 29.37, 29.29, 29.27, 29.19, 29.08, 29.02, 28.69, 27.08, 26.75, 25.97, 25.36, 25.02, 24.81, 24.61, 23.53, 22.72, 22.70, 14.14; MS-ESI (m/z): 752 (M+H)$^+$.

Example 2

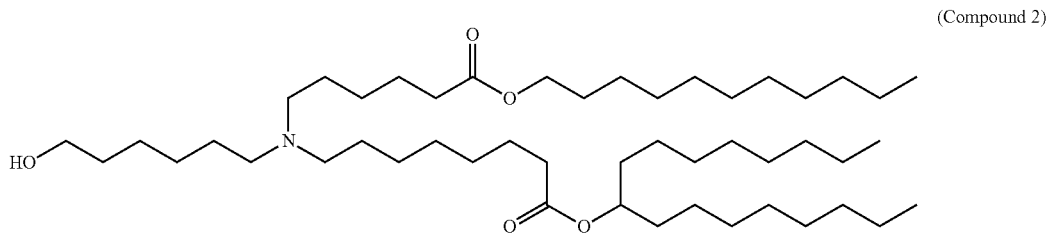 [SMILES: CCCCCCCCCCCOC(=O)CCCCCN(CCCCCCO)CCCCCCCC(=O)OC(CCCCCCCC)CCCCCCCC]

(Compound 2)

The preparation method is identical with that of compound 1, using 6-amino-1-hexanol as raw material to obtain oil compound 2: $^1$H NMR (500 MHz, CDCl$_3$) δ 4.86-4.81 (m, 1H), 4.04 (t, J=6.8 Hz, 2H), 3.63 (t, J=6.4 Hz, 2H), 2.99-2.94 (brs, 6H), 2.29 (dt, J=23.7, 4H), 1.87-1.75 (m, 7H), 1.69-1.55 (m, 8H), 1.51-1.24 (m, 55H), 0.86 (t, J=6.8 Hz, 9H); $^{13}$C NMR (151 MHz, CDCl$_3$) δ 173.58, 173.44, 74.37, 64.80, 62.41, 52.57, 52.49, 52.47, 34.61, 34.23, 33.92, 32.29, 32.01, 31.97, 29.70, 29.63, 29.61, 29.43, 29.37, 29.35, 29.00, 28.83, 28.74, 26.79, 26.55, 26.45, 26.03, 25.43, 25.17, 24.96, 24.32, 23.25, 23.19, 22.78, 14.22; MS-ESI (m/z): 766 (M+H)$^+$.

Example 3

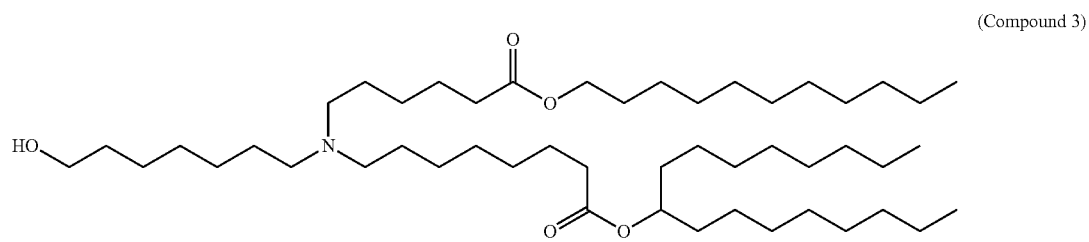 [SMILES: CCCCCCCCCCCOC(=O)CCCCCN(CCCCCCCO)CCCCCCCC(=O)OC(CCCCCCCC)CCCCCCCC]

(Compound 3)

The preparation method is identical with that of compound 1, using 7-amino-1-heptanol as raw material to obtain oil compound 3: $^1$H NMR (500 MHz, CDCl$_3$) δ 4.83-4.81 (m, 1H), 4.02 (t, J=6.8 Hz, 2H), 3.59 (t, J=6.6 Hz, 2H), 2.57 (brs, 6H), 2.28-2.22 (m, 4H), 1.81 (brs, 1H), 1.62-1.47 (m, 15H), 1.30-1.22 (m, 56H), 0.84 (t, J=6.8 Hz, 9H); MS-ESI (m/z): 780 (M+H)$^+$.

Example 4

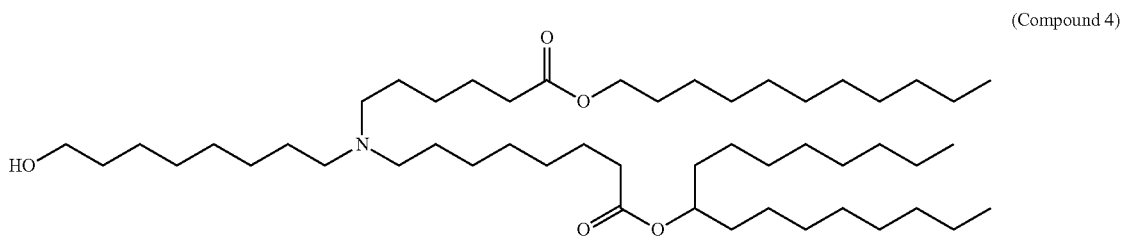 [SMILES: CCCCCCCCCCCOC(=O)CCCCCN(CCCCCCCCO)CCCCCCCC(=O)OC(CCCCCCCC)CCCCCCCC]

(Compound 4)

The preparation method is identical with that of compound 1, using 8-amino-1-octanol as raw material to prepare oil compound 4: $^1$H NMR (500 MHz, CDCl$_3$) δ 4.85-4.80 (m, 1H), 4.02 (t, J=6.8 Hz, 2H), 3.59 (t, J=6.6 Hz, 2H), 2.58 (brs, 6H), 2.28-2.22 (m, 4H), 1.81 (BRS, 1H), 1.64-1.46 (m, 15H), 1.29-1.22 (m, 58H), 0.84 (t, J=6.8 Hz, 9H); $^{13}$C NMR (126 MHz, CDCl$_3$) δ 173.71, 173.63, 74.21, 64.58, 62.84, 53.53, 34.69, 34.20, 32.79, 31.96, 31.92, 29.66, 29.64, 29.59, 29.56, 29.38, 29.31, 29.16, 28.72, 27.27, 26.94, 25.99, 25.72, 25.37, 24.77, 22.74, 22.72, 14.15; MS-ESI (m/z): 794 (M+H)$^+$.

Example 5

(Compound 5)

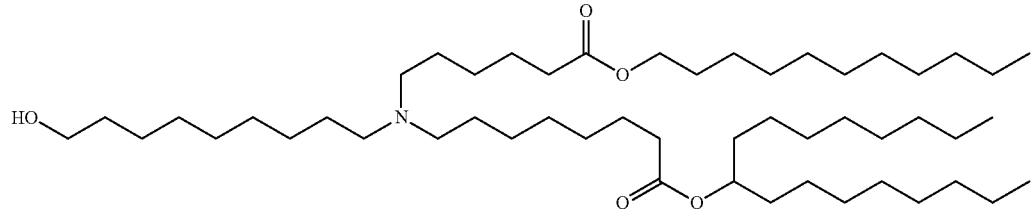

The preparation method is identical with that of compound 1, using 9-amino-1-nonanol as raw material to obtain oil compound 5: $^1$H NMR (500 MHz, CDCl$_3$) δ 4.85-4.81 (m, 1H), 4.02 (t, J=6.8 Hz, 2H), 3.59 (t, J=6.6 Hz, 2H), 2.56 (brs, 6H), 2.28-2.21 (m, 4H), 1.81 (brs, 1H), 1.62-1.47 (m, 15H), 1.31-1.20 (m, 60H), 0.84 (t, J=6.8 Hz, 9H); MS-ESI (m/z): 808 (M+H)$^+$.

Example 6

(Compound 6)

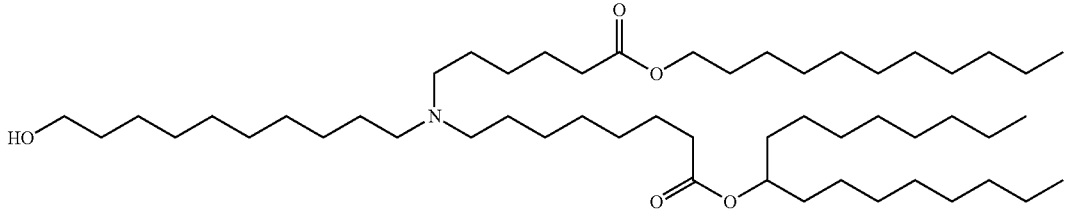

The preparation method is identical with that of compound 1, using 10-amino-1-n-decanol as raw material to prepare oil compound 6: $^1$H NMR (500 MHz, CDCl$_3$) δ 4.86-4.81 (m, 1H), 4.03 (t, J=6.8 Hz, 2H), 3.60 (q, J=6.2 Hz, 2H), 2.39 (s, 6H), 2.29-2.23 (m, 4H), 1.72-1.69 (m, 1H), 1.64-1.56 (m, 6H), 1.55-1.52 (m, 1H), 1.51-1.40 (m, 7H), 1.34-1.23 (m, 63H), 0.85 (t, J=6.8 Hz, 9H); $^{13}$C NMR (126 MHz, CDCl$_3$) δ 173.89, 173.69, 74.17, 64.51, 62.95, 54.14, 53.96, 34.78, 34.41, 34.23, 32.91, 31.98, 31.94, 29.68, 29.66, 29.63, 29.61, 29.58, 29.51, 29.41, 29.36, 29.34, 29.31, 29.29, 28.74, 27.65, 27.55, 27.23, 26.01, 25.86, 25.39, 25.20, 22.75, 22.73, 14.17; MS-ESI (m/z): 822 (M+H)$^+$.

Example 7

(Compound 7)

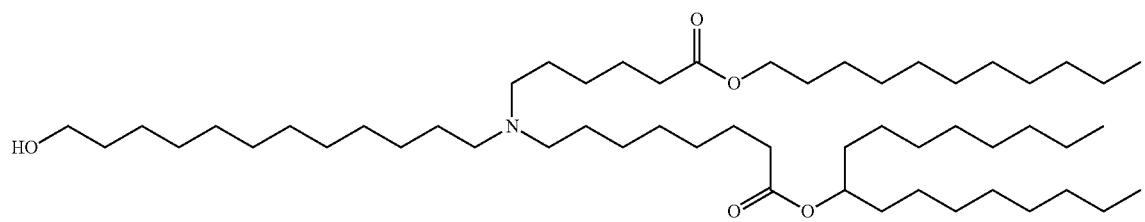

The preparation method is identical with that of compound 1, using 12-amino-1-dodecanol as raw material to obtain oil compounds 7: $^1$H NMR (500 MHz, CDCl$_3$) δ 4.85-4.80 (m, 1H), 4.02 (t, J=6.8 Hz, 2H), 3.59 (t, J=6.6 Hz, 2H), 2.51 (brs, 6H), 2.28-2.23 (m, 4H), 1.63-1.57 (m, 5H), 1.54-1.45 (m), 9H), 1.33-1.22 (m, 68H), 0.85 (t, J=6.7 Hz, 9H); $^{13}$C NMR (151 MHz, CDCl$_3$) δ 173.77, 173.66, 74.19, 64.56, 62.97, 53.74, 34.71, 34.28, 34.21, 32.89, 31.97, 31.93, 29.66, 29.64, 29.59, 29.57, 29.49, 29.39, 29.32, 29.30, 29.22, 29.20, 28.72, 27.48, 27.36, 27.03, 26.00, 25.84, 25.38, 25.12, 24.85, 22.74, 22.73, 14.17; MS-ESI (m/z): 850 (M+H)$^+$.

Example 8

(Compound 8)

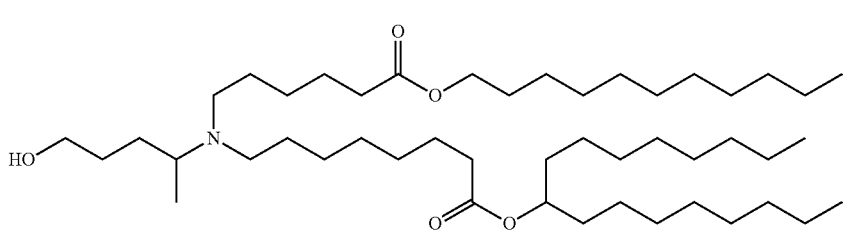

4-amino-1-pentanol (88 mg, 0.85 mmol) and DIEA (213 μL, 1.29 mmol) were added to the solution of compound A (200 mg, 0.43 mmol) in ethanol (5 mL), and heated at reflux for 20 hours. The reaction was monitored by TLC and cooled to room temperature after it was complete. An equal volume of water was added to the reaction solution for dilution, followed by ethyl acetate extraction (10 mL×3), concentration, and silica gel column chromatography (dichloromethane:methanol=10:1) to obtain compound B-1, X=CH$_3$CH(CH$_2$)$_3$ (151 mg, yield 75%).

5-fold equivalent compounds C (367 mg, 1.05 mmol), K$_2$CO$_3$ (145 mg, 1.05 mmol) and KI (17 mg, 0.21 mmol) were added to a mixed solvent of acetonitrile and cyclopentyl methyl ether (cyclopentyl methyl ether:acetonitrile=2:1, 3 mL) of compound B-1 (100 mg, 0.1 mmol), then heated at 90° C. for 24 hours. The reaction was monitored by TLC, and cooled to room temperature after it was complete. The reaction solution was diluted with water, then extracted with ethyl acetate (10 mL×3), concentrated, and chromatographed by silica gel column (dichloromethane:methanol=20:1) to obtain oil compound 8 (50 mg, yield 32%): $^1$H NMR (600 MHz, CDCl$_3$) δ 4.84-4.79 (m, 1H), 4.01-3.99 (t, J=6.8 Hz, 2H), 3.61-3.58 (t, J=6.2 Hz, 2H), 3.26 (brs, 1H), 2.70-2.66 (m, 2H), 2.43 (brs, 2H), 2.30-2.24 (m, 4H), 1.71-1.24 (m, 64H), 1.07 (d, J=6.2 Hz, 3H), 0.85-0.82 (m, 9H); $^{13}$C NMR (126 MHz, CDCl$_3$) δ 173.77, 173.60, 74.23, 67.66, 62.13, 53.26, 53.11, 34.64, 34.17, 34.11, 32.07, 31.94, 31.90, 31.88, 29.63, 29.56, 29.37, 29.29, 29.19, 29.08, 29.02, 28.69, 27.08, 25.97, 25.36, 25.02, 24.81, 24.61, 22.72, 22.70, 15.21, 14.14; MS-ESI (m/z): 752 (M+H)$^+$.

Example 9

(Compound 9)

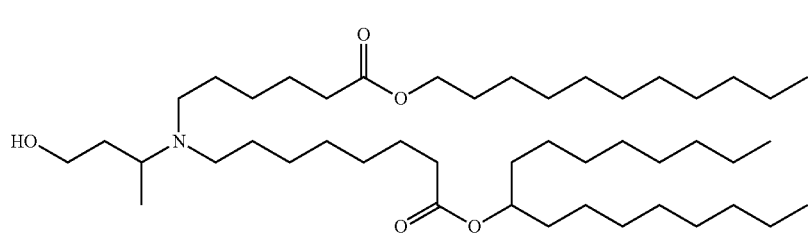

The preparation method is identical with that of compound 8, using 6-amino-1-hexanol as raw material to obtain oil compound 9: $^1$H NMR (600 MHz, CDCl$_3$) δ 4.84-4.79 (m, 1H), 4.01-3.99 (t, J=6.8 Hz, 2H), 3.61-3.58 (t, J=6.2 Hz, 2H), 3.26 (brs, 1H), 2.70-2.66 (m, 2H), 2.43 (brs, 2H), 2.30-2.24 (m, 4H), 1.71-1.24 (m, 62H), 1.07 (d, J=6.2 Hz, 3H), 0.85-0.82 (m, 9H); $^{13}$C NMR (126 MHz, CDCl$_3$) δ 173.73, 173.71, 74.27, 64.62, 59.44, 56.24, 39.42, 34.83, 34.42, 34.30, 32.25, 32.13, 29.77, 29.68, 29.49, 29.40, 29.33, 28.91, 27.47, 27.16, 26.08, 25.24, 25.06, 24.62, 20.71, 14.24; MS-ESI (m/z): 738 (M+H)$^+$.

Example 10

(Compound 10)

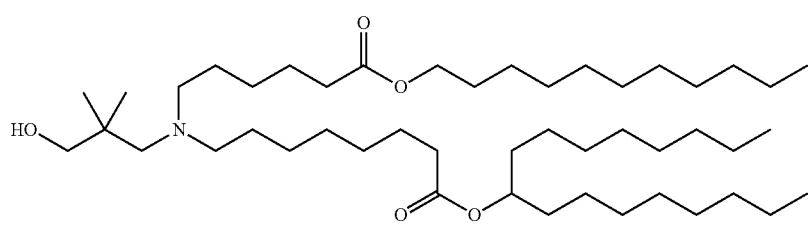

The preparation method is identical with that of compound 8, using 3-amino-2,2-dimethyl-1-propanol as raw material to prepare oil compound 10: $^1$H NMR (600 MHz, CDCl$_3$) δ 4.84-4.79 (m, 1H), 4.01 (t, J=6.8 Hz, 2H), 3.48 (s, 2H), 3.06 (s, 2H), 2.70-2.66 (m, 2H), 2.43 (brs, 2H), 2.30-2.24 (m, 4H), 1.71-1.24 (m, 63H), 0.92 (s, 6H), 0.85-0.82 (m, 9H); $^{13}$C NMR (126 MHz, CDCl$_3$) δ 173.85, 173.73, 74.27, 64.62, 56.44, 56.24, 35.44, 34.83, 34.42, 34.30, 32.05, 32.01, 29.73, 29.68, 29.47, 29.40, 29.33, 28.81, 27.47, 27.16, 26.08, 25.47, 25.24, 24.62, 22.81, 14.24; MS-ESI (m/z): 752 (M+H)$^+$.

Example 11

(Compound 11)

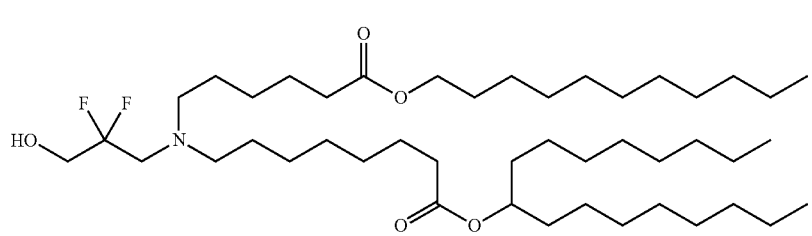

The preparation method is identical with that of compound 8, using 3-amino-2,2-difluoro-1-propanol as raw material to prepare oil compound 11: $^1$H NMR (600 MHz, CDCl$_3$) δ 4.84-4.79 (m, 1H), 4.01 (t, J=6.8 Hz, 2H), 3.83 (t, J=13 Hz, 2H), 3.06 (t, J=13 Hz, 2H), 2.70-2.66 (m, 2H), 2.43 (brs, 2H), 2.30-2.24 (m, 4H), 1.71-1.24 (m, 63H), 0.92 (s, 6H), 0.85-0.82 (m, 9H); MS-ESI (m/z): 760 (M+H)$^+$.

Example 12

(Compound 12)

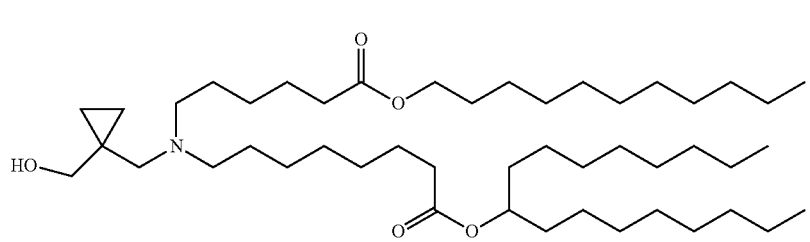

The preparation method is identical with that of compound 8, using 1-aminomethyl-cyclopropylmethanol as raw material to prepare oil compound 12: $^1$H NMR (600 MHz, CDCl$_3$) δ 4.84-4.79 (m, 1H), 4.01 (t, J=6.8 Hz, 2H), 3.41 (s, 2H), 2.70-2.66 (m, 2H), 2.43 (brs, 2H), 2.26 (s, 2H), 2.30-2.24 (m, 4H), 1.71-1.24 (m, 63H), 0.85-0.82 (m, 9H), 0.45-0.20 (m, 4H); $^{13}$C NMR (151 MHz, CDCl$_3$) δ 173.80, 173.67, 74.18, 71.61, 64.55, 62.76, 54.10, 53.91, 34.77, 34.36, 34.25, 32.01, 31.96, 29.70, 29.68, 29.63, 29.60, 29.43, 29.36, 29.33, 29.26, 28.76, 27.43, 27.11, 26.03, 25.42, 25.20, 25.01, 22.78, 22.76, 19.34, 14.20, 9.66; MS-ESI (m/z): 750 (M+H)$^+$.

CDCl$_3$) δ 4.84-4.79 (m, 1H), 4.01 (t, J=6.8 Hz, 2H), 2.70-2.66 (m, 2H), 2.43 (brs, 2H), 2.28 (s, 2H), 2.30-2.24 (m, 4H), 1.71-1.24 (m, 63H), 0.85-0.82 (m, 9H), 0.62-0.41 (m, 4H); $^{13}$C NMR (126 MHz, CDCl$_3$) δ 173.97, 173.77, 74.25, 66.40, 64.58, 53.23, 53.07, 45.05, 34.88, 34.54, 34.31, 32.06, 32.02, 29.74, 29.69, 29.65, 29.58, 29.48, 29.44, 29.41, 29.39, 28.82, 27.48, 27.16, 26.09, 25.47, 25.29, 25.13, 22.81, 14.26, 14.23, 11.88; MS-ESI (m/z): 736 (M+H)$^+$.

Example 15

(Compound 15)

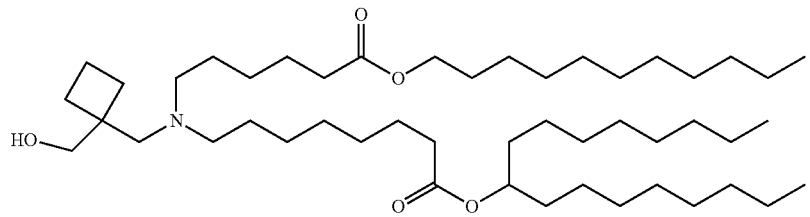

Example 13

(Compound 13)

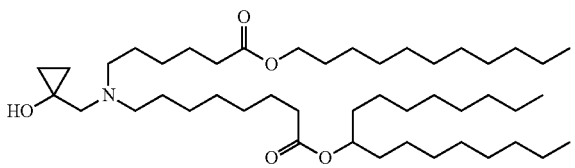

The preparation method is identical with that of compound 8, using 1-(aminomethyl)cyclopropanol as raw material to prepare oil compound 13, $^1$H NMR (600 MHz, CDCl$_3$) δ 4.84-4.79 (m, 1H), 4.01 (t, J=6.8 Hz, 2H), 2.70-2.66 (m, 2H), 2.43 (brs, 2H), 2.16 (s, 2H), 2.30-2.24 (m, 4H), 1.71-1.24 (m, 63H), 0.85-0.82 (m, 9H), 0.62-0.41 (m, 4H); $^{13}$C NMR (126 MHz, CDCl$_3$) δ 173.83, 173.71, 74.27, 64.63, 60.92, 53.99, 53.79, 52.35, 34.80, 34.38, 34.29, 32.04, 32.00, 29.72, 29.67, 29.46, 29.40, 29.37, 29.33, 29.30, 28.80, 27.37, 27.02, 26.45, 26.29, 26.07, 25.46, 25.23, 24.95, 22.80, 14.23, 11.42; MS-ESI (m/z): 736 (M+H)$^+$.

Example 14

(Compound 14)

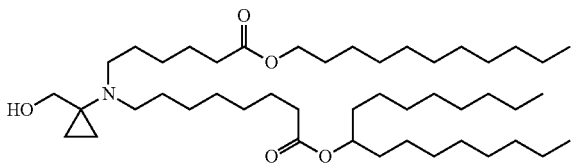

The preparation method is identical with that of compound 8, using 1-(aminocyclopropyl)methanol as raw material to prepare oil compound 14, $^1$H NMR (600 MHz, The preparation method is identical with compound 8, using 1-aminomethyl-cyclobutylmethanol as raw material to prepare oil compound 15: $^1$H NMR (600 MHz, CDCl$_3$) δ 4.84-4.79 (m, 1H), 4.01 (t, J=6.8 Hz, 2H), 3.48 (s, 2H), 3.06 (s, 2H), 2.70-2.66 (m, 2H), 2.43 (brs, 2H), 2.30-2.24 (m, 4H), 1.71-1.24 (m, 63H), 1.70-1.42 (m, 6H), 0.85-0.82 (m, 9H); $^{13}$C NMR (151 MHz, CDCl$_3$) δ 173.77, 173.64, 74.15, 70.83, 65.93, 64.52, 54.93, 54.73, 41.68, 34.74, 34.33, 34.24, 31.99, 31.95, 29.68, 29.66, 29.61, 29.58, 29.41, 29.34, 29.32, 29.23, 29.17, 28.74, 27.38, 27.06, 26.48, 26.26, 26.02, 25.40, 25.18, 24.97, 22.76, 22.75, 16.83, 14.18; MS-ESI (m/z): 764 (M+H)$^+$.

Example 16: Preparation of Reporter Gene Luciferase mRNA 1.1 Plasmid Linearization The reporter plasmid pUC57-luc contains the T7 promoter, 5' UTR, luciferase sequence, 3' UTR, and polyA tail, with a SapI digestion site after the last A of the polyA tail. Total 50 μL: plasmid to be tested 10 μg, restriction enzyme Sap I (10000 U/mL) 1 μL, 10× Cutsmart buffer 5 μL, and remaining ddH$_2$O. Restriction enzyme Sap I and 10× Cutsmart buffer are companion products, NEB, catalog number R0569L. The reaction conditions were 37° C., 3 h. After the reaction was completed, 2 μL of digestion product was taken and 1% agarose gel electrophoresis was performed to detect the linearization of the plasmid. After confirming that digestion has been completed, the linearized plasmid was collected using the Rapid DNA Product Purification Kit (Conway Century, CW2301M).

1.2 In Vitro Transcription

Linearized plasmids were used as templates for in vitro transcription with high-yield T7 RNA transcription kits. The high yield T7 RNA transcription kit, product name High Yield T7 RNA Synthesis Kit, was purchased from Shanghai Zhaowei Technology Development Co., Ltd., catalog number ON-040; 5× buffer, 100 mM ATP solution, 100 mM CTP solution, 100 mM GTP solution, mixed enzyme, DNase I, ammonium acetate stop solution, lithium chloride (LiCl) precipitant are all components in the high-yield T7 RNA transcription kit. 100 mM ψUTP solution, full name N1-Me-pUTP, 100 mM, was purchased from Shanghai Zhaowei Technology Development Co., Ltd., catalog number R5-027.

Specific steps of in vitro transcription: firstly, prepare the reaction system, mix well and react at 37° C. for 3 h; then, add 1 μL of DNase I (content 1 U) and react at 37° C. for 15 min; and then add 15 μL of ammonium acetate stop solution.

Reaction system: 4 μL of 5× buffer, 2 μL of 100 mM ATP solution, 1 μL of 100 mM ψUTP solution, 2 μL of 100 mM CTP solution, 2 μL of 100 mM GTP solution, 2 μL of mixed enzyme, linearized plasmid (DNA content of 500 ng-1 μg), nuclease-free water replenished to 20 μL.

1.3 RNA Purification

To the in vitro transcription reaction system was added ⅓ volume of 7.5 M LiCl (with a final concentration of 2.5 M) and leave at −20° C. for 30 min. Centrifuge at 12,000 g for 15 min, pellet the RNA at the bottom, and discard the supernatant. The RNA was washed with 1 mL of 70% ethanol, centrifuged at 12,000 g for 5 min, and the supernatant was discarded. After drying, 50 μL of RNase-free water was added to dissolve the pellet and perform mRNA quantification using a UV spectrophotometer to obtain capped in vitro transcribed mRNA.

Example 17: mRNA-LNP Encapsulation

The mRNA stock solution was dispersed in 20 mM acetic acid solution (pH 5.0) to a final concentration of 200 μg/mL (aqueous phase). A fat mixture (oil phase) was obtained by mixing under a molar ratio of the exemplary compound: cholesterol:DSPC:DMG-PEG2000=50:38.5:10:1.5. The flow rate of the aqueous phase and the oil phase was controlled by T mixed flow, and the mRNA and lipid mixture were mixed under the volume ratio of 3:1 to obtain LNP-encapsulated mRNA. The encapsulated LNP was diluted 10-fold with buffer, then concentrated by ultrafiltration, and the dilute was displaced, and finally the LNP was concentrated to mRNA being 200 g/mL, and the pH of the LNP was adjusted to about 7-8. Finally, the Ribogreen kit and 10% OTG were used as demulsifiers to detect the total content of mRNA and the content of free LNP, and the encapsulation rate of LNP was calculated. The LNP final product was diluted 10-fold with diluent, added 1 mL into a particle size cell, and placed on the Malvern ZetaSizer instrument to detect the particle size and PDI of LNP. The results are shown in Table 1.

TABLE 1

Characterization data of LNP of exemplary compounds.

| No. | Particle size (nm) | PDI | Encapsulation rate |
| --- | --- | --- | --- |
| Example 1 | 72.68 | 0.0892 | 96% |
| Example 2 | 72.02 | 0.0862 | 96% |
| Example 3 | 71.55 | 0.0835 | 94% |
| Example 4 | 70.42 | 0.0816 | 93% |
| Example 5 | 70.67 | 0.0865 | 91% |
| Example 6 | 70.88 | 0.0992 | 94% |
| Example 7 | 72.73 | 0.0987 | 92% |
| Example 8 | 94.2 | 0.2303 | 54.55% |
| Example 9 | 72.26 | 0.1102 | 97.55% |
| Example 10 | 98.2 | 0.1836 | 57.14% |
| Example 11 | 98.41 | 0.2522 | 57.25% |
| Example 12 | 78.07 | 0.2337 | 81.12% |
| Example 13 | 68.87 | 0.149 | 89.94% |
| Example 14 | 68.31 | 0.145 | 88.12% |

TABLE 1-continued

Characterization data of LNP of exemplary compounds.

| No. | Particle size (nm) | PDI | Encapsulation rate |
| --- | --- | --- | --- |
| Example 15 | 95.7 | 0.368 | 60.43% |
| SM102 | 92.16 | 0.1296 | 95% |

Example 18: Detection of Reporter Gene Expression in Mice In Vivo

The prepared LNP-encapsulated mRNA solution was diluted with PBS buffer to obtain the solution for injection. BALB/c female mice at about 20 g were injected with injection solution at the quadriceps muscle site of mice with an insulin syringe, and each mouse was injected with 50 μL. Two doses were designed: one dose of "5 μg mRNA per 50 μL of injection solution" and the other dose of "14 μg mRNA per 50 μL of injection solution". BALB/c female mice at about 20 g are injected with PBS buffer at the quadriceps muscle site of mice with an insulin syringe, and each mouse was injected with 50 μL.

After the mice were injected for 24 h, in vivo expression of Luciferase was detected with Perkinelmer's IVIS. The substrate was D-luciferin Sodium salt (GOLDBIO, LUCNA-1G), which was formulated into a concentration of 15 mg/mL with normal saline, filtered and sterilized with a 0.22 μm filter membrane, and stored at −20° C. in aliquots protected from light. Before imaging, each mouse at about 20 g was intraperitoneally injected with 200 μL of substrate solution for 10-20 minutes, and then was anesthetized with isoflurane gas and placed prone on the imaging plate to detect the fluorescence of the animal in vivo, and the results are shown in Table 2.

TABLE 2

Expression levels of cationic lipid LNP-delivering luciferase mRNA in mice in vivo

| No. | Average fluorescence intensity P/s/cm$^2$/sr | Standard deviation |
| --- | --- | --- |
| Example 1 | 1.218E+06 | 2.02E+05 |
| Example 2 | 1.144E+06 | 1.99E+05 |
| Example 3 | 8.55E+05 | 1.83E+05 |
| Example 4 | 5.47E+05 | 0.97E+05 |
| Example 5 | 5.67E+05 | 0.88E+05 |
| Example 6 | 5.08E+05 | 0.24E+05 |
| Example 7 | 4.73E+05 | 0.12E+05 |
| Example 8 | 1.17E+03 | 4.42E+02 |
| Example 9 | 3.74E+05 | 3.95E+05 |
| Example 10 | 7.37E+03 | 3.05E+03 |
| Example 11 | 1.39E+03 | 5.55E+02 |
| Example 12 | 3.62E+03 | 2.16E+03 |
| Example 13 | 2.78E+05 | 1.37E+05 |
| Example 14 | 1.91E+03 | 4.15E+02 |
| Example 15 | 1.57E+03 | 6.41E+02 |
| SM102 | 1.112E+06 | 2.11E+05 |

Example 19: Acute Toxicity Analysis of Lipid Molecules in BALB/c Female Mice

Figure 4A:
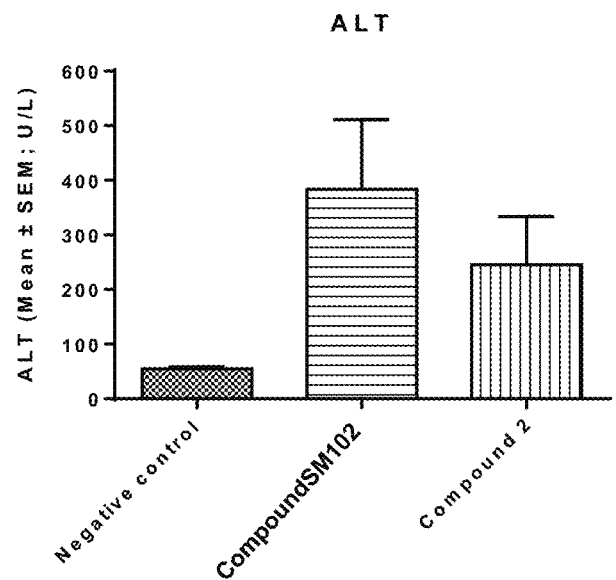
FIGS. 4A and 4B illustrate the effect of compound 2 on serum ALT and AST levels.
Figure 4B:
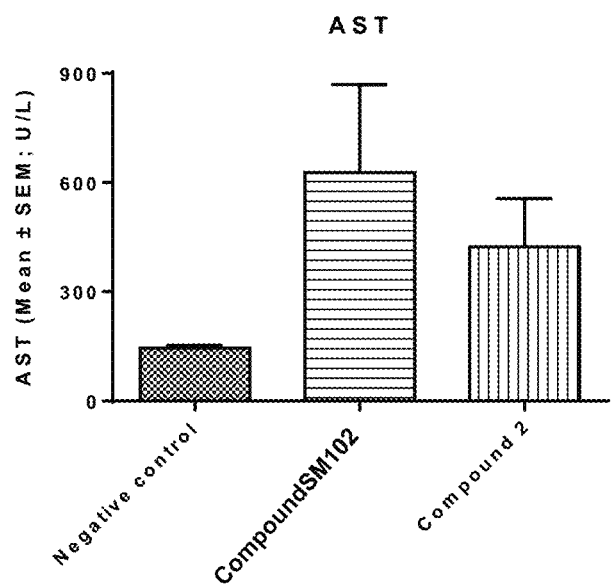

In order to investigate the biosafety of exemplary compounds, we analyzed the acute toxicity of the compounds of the present invention. The BALB/c female mice were enrolled in the experiment, 10 in each group, and the high and low concentration groups were set to be 50 μg/pc and 150 µg LNP/pc, respectively. SM102 was used as the positive control and PBS as the negative control. After the mouse was injected for 24 h, about 100 µL of blood is collected into the blood collection containing EDTA through the orbital blood collection, and after sampling, gently inverted up and down several times to fully mix the blood with the anticoagulant. Samples was stored at 4° C., not in direct contacting with ice packs, not violent impacting, and the test results are shown in Table 3 and Table 4.

injected with 3 mg/kg of mRNA encoding Luciferase through the tail vein, fasted overnight with supplying water, and whole blood was collected 24 hours after injection, and serum was isolated. The concentration of ALT and AST in the serum of each rat was detected with a fully automated biochemical analyzer, and the test results are shown in FIGS. 4A and 4B.

The results showed that the elevation effect of compound 2 on serum ALT and AST was significantly lower than these

TABLE 3

Acute toxicity analysis of cationic lipid LNP (low dose group)

| Ave(SD) | Aspartate aminotransferase U/L | Alanine aminotransferase U/L | Alkaline phosphatase (ALP) U/L | γ-Glutamyltransferase (GGT) U/L | Total bilirubin (TBIL) (mmol/L) | Creatinine (µmol/L) |
|---|---|---|---|---|---|---|
| Example 1 | 109.92 (8.68) | 33.46 (3.54) | 114.38 (13.53) | 0.22 (0.33) | 1.18 (0.13) | 13.8 (13.73) |
| Example 2 | 111.74 (20.96) | 35.32 (2.51) | 113.3 (11.96) | 0.40 (0.37) | 1.22 (0.20) | 12.6 (1.36) |
| Example 7 | 109.54 (7.77) | 33.56 (5.17) | 107.58 (12.54) | 0.06 (0.12) | 1.18 (0.16) | 13.6 (1.36) |
| Example 9 | 107.55 (8.14) | 35.44 (3.67) | 115.29 (11.87) | 0.24 (0.37) | 1.21 (0.19) | 14.2 (4.79) |
| Example 13 | 110.27 (10.05) | 36.19 (3.01) | 111.74 (12.88) | 0.38 (0.41) | 1.18 (0.23) | 13.5 (2.06) |
| SM102 | 121.4 (8.30) | 36.04 (2.93) | 131.7 (6.85) | 0.41 (0.24) | 1.15 (0.15) | 14.6 (2.06) |
| PBS | 98.32 (5.62) | 34.04 (4.58) | 168.58 (19.1) | 0.14 (0.05) | 1.43 (0.12) | 17.4 (2.87) |

TABLE 4

Acute toxicity analysis of cationic lipid LNP (high dose group)

| Ave(SD) | Aspartate aminotransferase U/L | Alanine aminotransferase U/L | Alkaline phosphatase (ALP) U/L | γ-Glutamyltransferase (GGT) U/L | Total bilirubin (TBIL) (mmol/L) | Creatinine (µmol/L) |
|---|---|---|---|---|---|---|
| Example 1 | 125.26 (4.23) | 38.16 (3.76) | 112.7 (13.93) | 0.12 (0.12) | 1.56 (0.19) | 12.4 (0.8) |
| Example 2 | 124.48 (14.18) | 41.54 (2.48) | 111.86 (8.15) | 0.20 (0.18) | 1.25 (0.13) | 12.6 (1.85) |
| Example 7 | 138.44 (10.54) | 39.92 (4.9) | 103.8 (8.21) | 0.22 (0.04) | 1.35 (0.1) | 12.2 (0.75) |
| Example 9 | 128.26 (3.23) | 37.25 (2.97) | 116.9 (14.11) | 0.18 (0.15) | 1.43 (0.22) | 12.1 (0.77) |
| Example 13 | 126.77 (12.46) | 39.99 (3.47) | 109.84 (7.25) | 0.18 (0.18) | 1.34 (0.21) | 12.4 (1.27) |
| SM102 | 145.96 (20.19) | 56.18 (38.13) | 116.88 (10.1) | 0.32 (0.22) | 1.44 (0.16) | 12.6 (0.8) |
| PBS | 108.50 (18.66) | 39.60 (3.05) | 173.92 (19.66) | 0.16 (0.05) | 1.15 (0.13) | 27.4 (22.84) |

The results show that compared with the control group, there were no significant changes in the six main toxicological indexes (creatinine, total bilirubin, aspartate aminotransferase, alanine aminotransferase, alkaline phosphatase and γ-glutamyl transpeptidase), preliminarily indicating the safety of these products. Taking the high-dose group as an example, compared with the SM102 group, the values of aspartate aminotransferase, alanine aminotransferase and γ-glutamyl transpeptidase decrease by 10-30%, indicating that the hepatic and renal toxicity of these products was further reduced, showing higher biological safety.

Example 20: Liver Injury Toxicity Analysis of Lipid Molecules in SD Rat

In order to further investigate the hepatic injury toxicity of exemplary compounds, we analyze the effect of the compounds of the present invention on serum alanine aminotransferase (ALT) and glutamate aminotransferase (AST) levels. The experimental 30 SD rats (15 females+15 males, purchased from Zhejiang Weitong Lihua Laboratory Animal Technology Co., Ltd.) were randomly divided into three groups, namely negative control group (PBS), SM102 group, and compound 2 group, each group of 5 female mice+5 male mice. According to body weight, each rat was of compound SM102, indicating that the liver injury toxicity was lower and the drug safety was better.

Example 21: In Vivo Expression Distribution Analysis

In order to investigate the distribution features of lipid-delivering mRNA in vivo, we analyzed the distribution features of the reporter luciferase mRNA of the compounds of the present invention in C57BL/6J mice after administration by a single intramuscular injection. The experimental 10 C57BL/6J mice were enrolled, male and female, each administered 50 µg, with SM102 as the control.

Animals in the negative control group were collected at 2 h and 336 h after administration, and animals in the test group were collected at 2 h, 6 h, 24 h, 48 h, 72 h, 120 h, 168 h, and 336 h after administration whole blood, bone marrow, liver, spleen, heart, kidney, inguinal lymph nodes, mesenteric lymph nodes, spleen, brain, stomach, small intestine, non-injection site muscle, injection site muscle tissue, etc. The RNA content in the samples at each time point was detected by RT-PCR, and the lower limit of quantification of the method was copies/reaction to reflect the distribution features in C57BL/6J mice.

Figure 2:
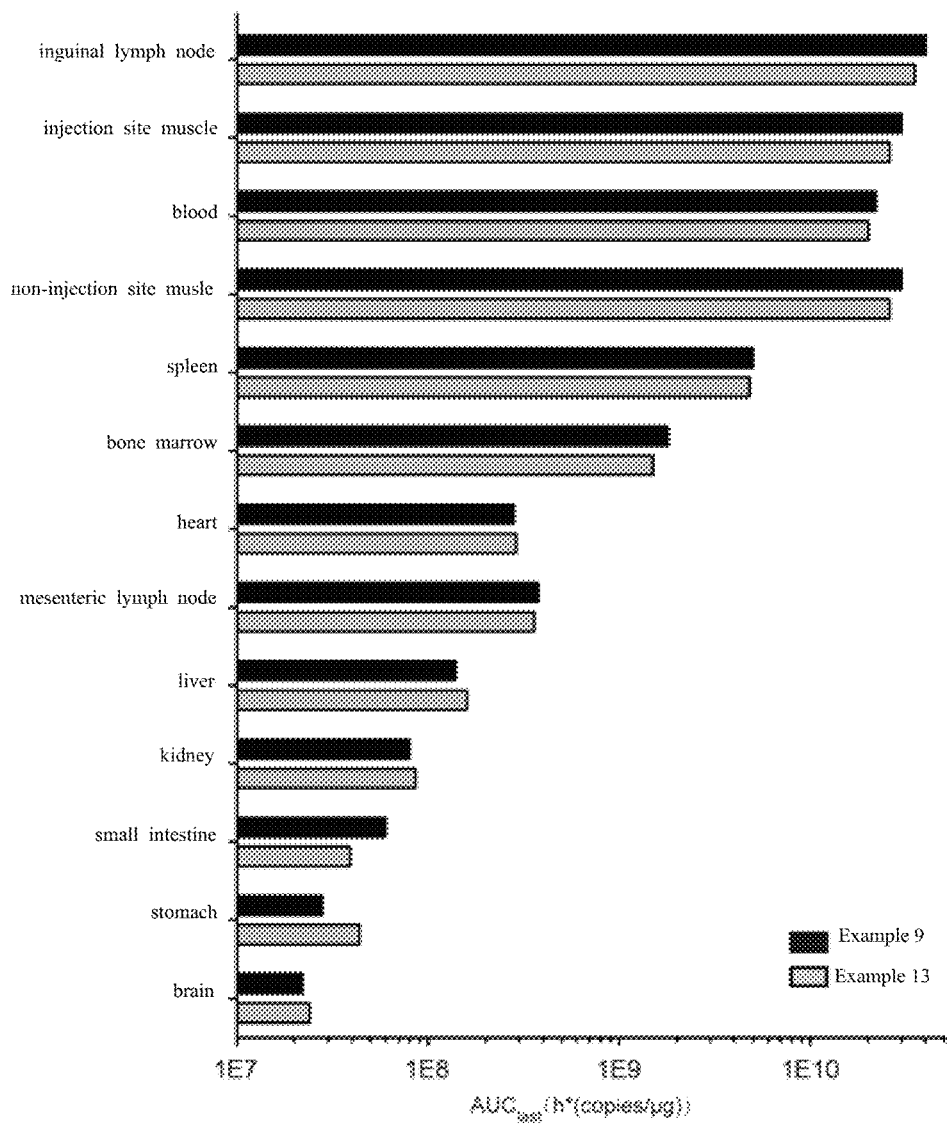
Figure 3A:
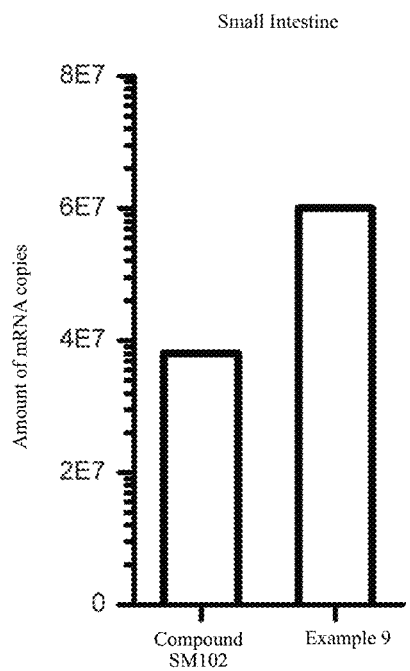
FIGS. 3A and 3B illustrate distribution of delivered mRNA in vivo.
Figure 3B:
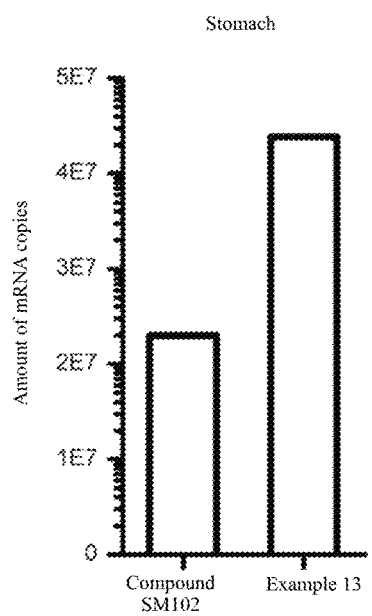

The results showed that in the animals injected with SM102, the exposure in tissues and organs was, from high to low, inguinal lymph nodes, injection site muscles, whole blood, non-injection site muscles, spleen, bone marrow, heart, mesenteric lymph nodes, liver, kidney, small intestine, and brain. In animals injected with lipid examples 1, 2, and 7, the exposure in tissue organs was, from high to low: injection site muscle, inguinal lymph nodes, whole blood, spleen, non-injection site muscle, bone marrow, heart, liver, mesenteric lymph nodes, kidney, small intestine and brain (see FIG. 1). In animals injected with lipid example 9, the exposure in tissue organs from high to low was: inguinal lymph nodes, injection site muscles, non-injection site muscles, whole blood, spleen, bone marrow, mesenteric lymph nodes, heart, liver, kidney, small intestine, stomach and brain. In animals injected with lipid example 13, the exposure in tissue organs from high to low was: inguinal lymph nodes, injection site muscles, non-injection site muscles, whole blood, spleen, bone marrow, mesenteric lymph nodes, heart, liver, kidneys, stomach, small intestine and brain (see FIG. 2). The results of the study showed that the distribution of mRNA delivered by Examples 1 and 2 is higher than SM102 in the circulatory system, immune system and muscle, but lower than SM102 in the liver, heart and kidney. Further, the mRNA delivered by the compound in Example 7 has a higher distribution in the stomach. This result suggests that compared with SM102, this class of lipids obtained in Examples 1 and 2 are more suitable as delivery carriers and more suitable for use in products such as vaccines, while reducing aggregation in the liver, heart and kidneys, and reducing their potential toxicity. It should be noted that compared with SM-102, the mRNA delivered by compound 9 has relatively higher level in the small intestine, while the mRNA delivered by compound 7 and compound 13 has relatively higher level in the stomach. Lipid compounds 7 and 13 have certain advantages in gastric delivery, and compound 9 has certain advantages in small intestine delivery.

Example 22: Pharmacokinetic Study

Figure 5:
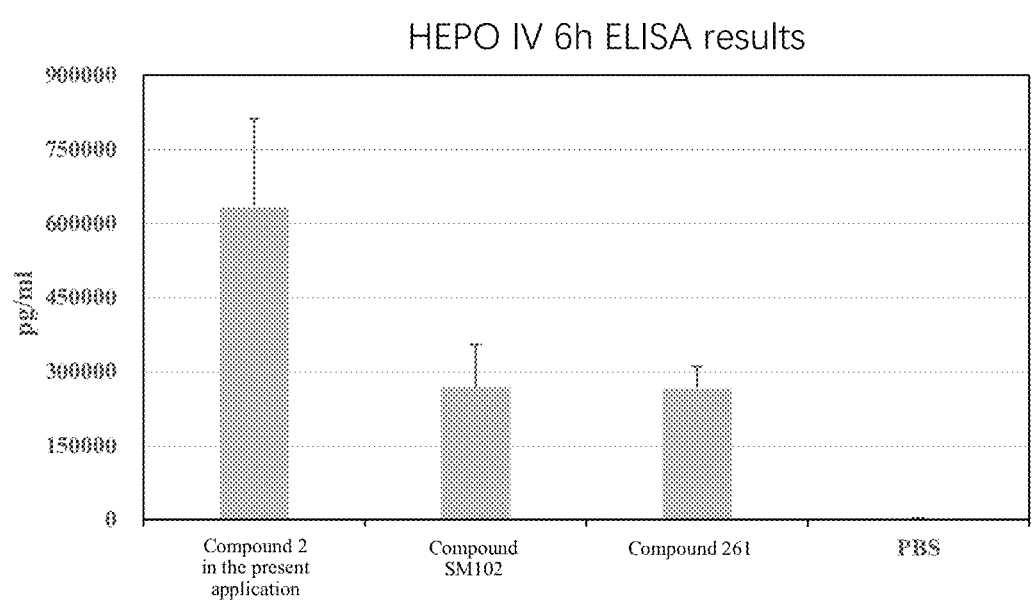
FIG. 5 illustrates the serum concentration of hEPO after administration of 5 μg of LNP (lipid nanoparticles) containing mRNA encoding hEPO for 6 h.

In order to investigate the pharmacokinetic properties of the compounds of the present invention, in particular their ability to deliver the active pharmaceutical ingredient as a carrier, we analyzed the effect of LNPs containing different compounds on the level of hEPO in serum. The experiment 20 of 6-8 weeks old female BALB/C mice (purchased from Zhejiang Weitong Lihua Laboratory Animal Technology Co., Ltd.) were enrolled, randomly divided into four groups of PBS, compound 2, compound SM102 and compound 261 (CN110520409A). Each mouse is injected with 5 μg of mRNA encoding hEPO through the tail vein, whole blood is collected at 6 h after injection, and serum is isolated. The hEPO concentration in the serum of each mouse was detected by reference to the instructions for the Elisa assay kit for hEPO and the results are shown in FIG. 5.

The results show that compared with compound SM102 and compound 261, the delivery carrier prepared by the exemplary compound 2 is significantly more efficient for drug delivery.

What is claimed is:

1. A long chain alkyl esteramine lipid compound having a structure of,

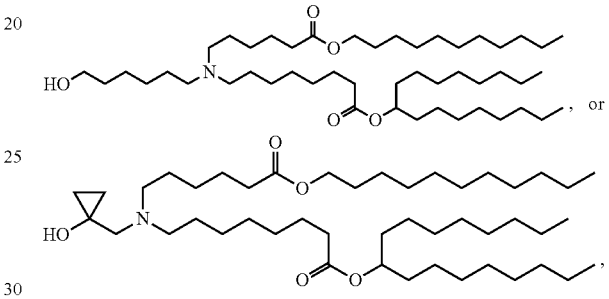

or a stereoisomer, solvate, or a pharmaceutically acceptable salt thereof.

2. A composition comprising a therapeutic or prophylactic agent and a carrier for delivering the therapeutic or prophylactic agent, wherein the carrier comprises the long chain alkyl esteramine lipid compound according to claim 1, or a stereoisomer, solvate, or a pharmaceutically acceptable salt thereof.

3. The composition according to claim 2, wherein the therapeutic or prophylactic agent comprises one or more of a nucleic acid molecule, peptide, protein or a small molecule compound.

* * * * *